(12) United States Patent
Kerr et al.

(10) Patent No.: US 9,028,492 B2
(45) Date of Patent: May 12, 2015

(54) SURGICAL INSTRUMENTS WITH REMOVABLE COMPONENTS

(75) Inventors: Duane E. Kerr, Loveland, CO (US); Allan J. Evans, Golden, CO (US); Arlan J. Reschke, Longmont, CO (US); Robert M. Sharp, Boulder, CO (US); William H. Nau, Jr., Longmont, CO (US); Glenn A. Horner, Boulder, CO (US); Mark J. Huseman, Broomfield, CO (US)

(73) Assignee: Covidien LP, Mansfield, MA (US)

( * ) Notice: Subject to any disclaimer, the term of this patent is extended or adjusted under 35 U.S.C. 154(b) by 878 days.

(21) Appl. No.: 13/212,343

(22) Filed: Aug. 18, 2011

(65) Prior Publication Data

US 2013/0046295 A1    Feb. 21, 2013

(51) Int. Cl.
*A61B 18/12* (2006.01)
*A61B 18/14* (2006.01)
*A61B 18/00* (2006.01)

(52) U.S. Cl.
CPC ..... *A61B 18/1445* (2013.01); *A61B 2018/0063* (2013.01); *A61B 2018/1455* (2013.01); *A61B 2018/1495* (2013.01)

(58) Field of Classification Search
CPC .............. A61B 18/1445; A61B 2018/0063; A61B 2018/1455; A61B 2018/1495
USPC ...................................... 606/48–52
See application file for complete search history.

(56) References Cited

U.S. PATENT DOCUMENTS

| D249,549 S | 9/1978 | Pike |
|---|---|---|
| D263,020 S | 2/1982 | Rau, III |
| D295,893 S | 5/1988 | Sharkany et al. |
| D295,894 S | 5/1988 | Sharkany et al. |
| D298,353 S | 11/1988 | Manno |

(Continued)

FOREIGN PATENT DOCUMENTS

| CN | 201299462 | 9/2009 |
|---|---|---|
| DE | 2415263 | 10/1975 |

(Continued)

OTHER PUBLICATIONS

U.S. Appl. No. 08/926,869, filed Sep. 10, 1997, James G. Chandler.

(Continued)

*Primary Examiner* — Michael Peffley
*Assistant Examiner* — Daniel Fowler

(57) ABSTRACT

A surgical instrument includes a handle coupled to a source of electrosurgical energy. A pair of opposed jaw members is operatively coupled to a distal end of the handle such that the jaw members selectively move between open and closed positions. A base supported on one of the jaw members includes a mechanical mating feature and an electrically conductive region in electrical communication with the source of electrosurgical energy. A selectively removable seal plate includes a complementarily engaging a mechanical mating feature and an electrically conductive region positioned to contact the electrically conductive region of the base when the mechanical mating features of the base and seal plate are engaged. The complimentarily-engaging mechanical mating features include a pair of spaced protrusions and a pair of spaced recesses open to opposing sides of the base or the seal plate such that the seal plate may be twisted onto the base.

6 Claims, 7 Drawing Sheets

(56) References Cited

U.S. PATENT DOCUMENTS

| | | | |
|---|---|---|---|
| D299,413 S | 1/1989 | DeCarolis | |
| D343,453 S | 1/1994 | Noda | |
| 5,304,203 A | 4/1994 | El-Mallawany et al. | |
| D348,930 S | 7/1994 | Olson | |
| D349,341 S | 8/1994 | Lichtman et al. | |
| D354,564 S | 1/1995 | Medema | |
| D358,887 S | 5/1995 | Feinberg | |
| 5,578,052 A | 11/1996 | Koros et al. | |
| 5,618,294 A | 4/1997 | Aust et al. | |
| D384,413 S | 9/1997 | Zlock et al. | |
| 5,665,100 A | 9/1997 | Yoon | |
| H1745 H | 8/1998 | Paraschac | |
| 5,814,043 A | 9/1998 | Shapeton | |
| D402,028 S | 12/1998 | Grimm et al. | |
| D408,018 S | 4/1999 | McNaughton | |
| D416,089 S | 11/1999 | Barton et al. | |
| 6,050,996 A | 4/2000 | Schmaltz et al. | |
| D424,694 S | 5/2000 | Tetzlaff et al. | |
| D425,201 S | 5/2000 | Tetzlaff et al. | |
| H1904 H | 10/2000 | Yates et al. | |
| 6,293,954 B1* | 9/2001 | Fogarty et al. | 606/151 |
| D449,886 S | 10/2001 | Tetzlaff et al. | |
| 6,329,778 B1 | 12/2001 | Culp et al. | |
| D453,923 S | 2/2002 | Olson | |
| D454,951 S | 3/2002 | Bon | |
| D457,958 S | 5/2002 | Dycus et al. | |
| D457,959 S | 5/2002 | Tetzlaff et al. | |
| 6,406,485 B1* | 6/2002 | Hossain et al. | 606/207 |
| H2037 H | 7/2002 | Yates et al. | |
| 6,464,704 B2 | 10/2002 | Schmaltz et al. | |
| D465,281 S | 11/2002 | Lang | |
| D466,209 S | 11/2002 | Bon | |
| 6,511,480 B1 | 1/2003 | Tetzlaff et al. | |
| 6,673,092 B1 | 1/2004 | Bacher | |
| D493,888 S | 8/2004 | Reschke | |
| D496,997 S | 10/2004 | Dycus et al. | |
| D499,181 S | 11/2004 | Dycus et al. | |
| D502,994 S | 3/2005 | Blake, III | |
| D509,297 S | 9/2005 | Wells | |
| D525,361 S | 7/2006 | Hushka | |
| D531,311 S | 10/2006 | Guerra et al. | |
| 7,118,570 B2 | 10/2006 | Tetzlaff et al. | |
| D533,274 S | 12/2006 | Visconti et al. | |
| D533,942 S | 12/2006 | Kerr et al. | |
| D535,027 S | 1/2007 | James et al. | |
| D538,932 S | 3/2007 | Malik | |
| D541,418 S | 4/2007 | Schechter et al. | |
| D541,611 S | 5/2007 | Aglassinger | |
| D541,938 S | 5/2007 | Kerr et al. | |
| D545,432 S | 6/2007 | Watanabe | |
| D547,154 S | 7/2007 | Lee | |
| 7,329,257 B2* | 2/2008 | Kanehira et al. | 606/52 |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| D582,038 S | 12/2008 | Swoyer et al. | |
| 7,641,653 B2 | 1/2010 | Dalla Betta et al. | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| D621,503 S | 8/2010 | Otten et al. | |
| D627,462 S | 11/2010 | Kingsley | |
| D628,289 S | 11/2010 | Romero | |
| D628,290 S | 11/2010 | Romero | |
| D630,324 S | 1/2011 | Reschke | |
| 2003/0018332 A1 | 1/2003 | Schmaltz et al. | |
| 2003/0109875 A1 | 6/2003 | Tetzlaff et al. | |
| 2005/0113828 A1 | 5/2005 | Shields et al. | |
| 2006/0253126 A1 | 11/2006 | Bjerken et al. | |
| 2007/0062017 A1 | 3/2007 | Dycus et al. | |
| 2007/0260241 A1 | 11/2007 | Dalla Betta et al. | |
| 2009/0131934 A1 | 5/2009 | Odom et al. | |
| 2010/0016857 A1 | 1/2010 | Mckenna et al. | |
| 2010/0228250 A1 | 9/2010 | Brogna | |
| 2010/0292691 A1 | 11/2010 | Brogna | |
| 2010/0305567 A1* | 12/2010 | Swanson | 606/49 |
| 2011/0072638 A1 | 3/2011 | Brandt et al. | |

FOREIGN PATENT DOCUMENTS

| | | |
|---|---|---|
| DE | 2514501 | 10/1976 |
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 10045375 | 10/2002 |
| DE | 10 2004 026179 | 12/2005 |
| DE | 20 2007 009165 | 10/2007 |
| DE | 20 2007 009317 | 10/2007 |
| DE | 20 2007 016233 | 3/2008 |
| DE | 19738457 | 1/2009 |
| DE | 10 2008 018406 | 7/2009 |
| EP | 1159926 | 12/2001 |
| EP | 2353535 A1 | 8/2011 |
| JP | 61-501068 | 9/1984 |
| JP | 6-502328 | 3/1992 |
| JP | 5-5106 | 1/1993 |
| JP | 5-40112 | 2/1993 |
| JP | 6-121797 | 5/1994 |
| JP | 6-285078 | 10/1994 |
| JP | 6-343644 | 12/1994 |
| JP | 6-511401 | 12/1994 |
| JP | 7-265328 | 10/1995 |
| JP | 8-56955 | 3/1996 |
| JP | 8-252263 | 10/1996 |
| JP | 8-317934 | 12/1996 |
| JP | 9-10223 | 1/1997 |
| JP | 9-122138 | 5/1997 |
| JP | 10-24051 | 1/1998 |
| JP | 11-070124 | 5/1998 |
| JP | 10-155798 | 6/1998 |
| JP | 2000-102545 | 9/1998 |
| JP | 11-47150 | 2/1999 |
| JP | 11-169381 | 6/1999 |
| JP | 11-192238 | 7/1999 |
| JP | 11-244298 | 9/1999 |
| JP | 2000-342599 | 12/2000 |
| JP | 2000-350732 | 12/2000 |
| JP | 2001-8944 | 1/2001 |
| JP | 2001-29356 | 2/2001 |
| JP | 2001-128990 | 5/2001 |
| JP | 2001-190564 | 7/2001 |
| JP | 2004-517668 | 6/2004 |
| JP | 2004-528869 | 9/2004 |
| SU | 401367 | 11/1974 |
| WO | WO 94/00059 | 1/1994 |
| WO | WO 99/23933 | 5/1999 |
| WO | WO 00/24330 | 5/2000 |
| WO | WO 00/36986 | 6/2000 |
| WO | WO 01/15614 | 3/2001 |
| WO | WO 01/54604 | 8/2001 |
| WO | WO 02/080793 | 10/2002 |
| WO | WO 2005/110264 | 11/2005 |

OTHER PUBLICATIONS

U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremcich.
U.S. Appl. No. 12/692,414, filed Jan. 22, 2010, Peter M. Mueller.
U.S. Appl. No. 12/696,592, filed Jan. 29, 2010, Jennifer S. Harper.
U.S. Appl. No. 12/696,857, filed Jan. 29, 2010, Edward M. Chojin.

(56) References Cited

OTHER PUBLICATIONS

U.S. Appl. No. 12/700,856, filed Feb. 5, 2010, James E. Krapohl.
U.S. Appl. No. 12/719,407, filed Mar. 8, 2010, Arlen J. Reschke.
U.S. Appl. No. 12/728,994, filed Mar. 22, 2010, Edward M. Chojin.
U.S. Appl. No. 12/748,028, filed Mar. 26, 2010, Jessica E.C. Olson.
U.S. Appl. No. 12/757,340, filed Apr. 9, 2010, Carine Hoarau.
U.S. Appl. No. 12/758,524, filed Apr. 12, 2010, Duane E. Kerr.
U.S. Appl. No. 12/759,551, filed Apr. 13, 2010, Glenn A. Horner.
U.S. Appl. No. 12/769,444, filed Apr. 28, 2010, Glenn A. Horner.
U.S. Appl. No. 12/770,369, filed Apr. 29, 2010, Glenn A. Horner.
U.S. Appl. No. 12/770,380, filed Apr. 29, 2010, Glenn A. Horner.
U.S. Appl. No. 12/770,387, filed Apr. 29, 2010, Glenn A. Horner.
U.S. Appl. No. 12/773,526, filed May 4, 2010, Duane E. Kerr.
U.S. Appl. No. 12/773,644, filed May 4, 2010, Thomas J. Gerhardt.
U.S. Appl. No. 12/786,589, filed May 25, 2010, Duane E. Kerr.
U.S. Appl. No. 12/791,112, filed Jun. 1, 2010, David M. Garrison.
U.S. Appl. No. 12/792,001, filed Jun. 2, 2010, Duane E. Kerr.
U.S. Appl. No. 12/792,008, filed Jun. 2, 2010, Duane E. Kerr.
U.S. Appl. No. 12/792,019, filed Jun. 2, 2010, Duane E. Kerr.
U.S. Appl. No. 12/792,038, filed Jun. 2, 2010, Glenn A. Horner.
U.S. Appl. No. 12/792,051, filed Jun. 2, 2010, David M. Garrison.
U.S. Appl. No. 12/792,068, filed Jun. 2, 2010, Glenn A. Horner.
U.S. Appl. No. 12/792,097, filed Jun. 2, 2010, Duane E. Kerr.
U.S. Appl. No. 12/792,262, filed Jun. 2, 2010, Jeffrey M. Roy.
U.S. Appl. No. 12/792,299, filed Jun. 2, 2010, Jeffrey M. Roy.
U.S. Appl. No. 12/792,330, filed Jun. 2, 2010, David M. Garrison.
U.S. Appl. No. 12/822,024, filed Jun. 23, 2010, Peter M. Mueller.
U.S. Appl. No. 12/821,253, filed Jun. 23, 2010, Edward M. Chojin.
U.S. Appl. No. 12/832,772, filed Jul. 8, 2010, Gary M. Couture.
U.S. Appl. No. 12/843,384, filed Jul. 26, 2010, David M. Garrison.
U.S. Appl. No. 12/845,203, filed Jul. 28, 2010, Gary M. Couture.
U.S. Appl. No. 12/853,896, filed Aug. 10, 2010, William H. Nau, Jr.
U.S. Appl. No. 12/859,896, filed Aug. 20, 2010, Peter M. Mueller.
U.S. Appl. No. 12/861,198, filed Aug. 23, 2010, James A. Gilbert.
U.S. Appl. No. 12/861,209, filed Aug. 23, 2010, William H. Nau, Jr.
U.S. Appl. No. 12/876,668, filed Sep. 7, 2010, Sara E. Anderson.
U.S. Appl. No. 12/876,680, filed Sep. 7, 2010, Peter M. Mueller.
U.S. Appl. No. 12/876,705, filed Sep. 7, 2010, Kristin D. Johnson.
U.S. Appl. No. 12/876,731, filed Sep. 7, 2010, Kristin D. Johnson.
U.S. Appl. No. 12/877,199, filed Sep. 8, 2010, Arlen J. Reschke.
U.S. Appl. No. 12/877,482, filed Sep. 8, 2010, Gary M. Couture.
U.S. Appl. No. 12/895,020, filed Sep. 30, 2010, Jeffrey M. Roy.
U.S. Appl. No. 12/896,100, filed Oct. 1, 2010, Ryan Artale.
U.S. Appl. No. 12/897,346, filed Oct. 4, 2010, Ryan Artale.
U.S. Appl. No. 12/906,672, filed Oct. 18, 2010, Kathy E. Rooks.
U.S. Appl. No. 12/915,809, filed Oct. 29, 2010, Thomas J. Gerhardt, Jr.
U.S. Appl. No. 12/947,352, filed Nov. 16, 2010, Jason L. Craig.
U.S. Appl. No. 12/947,420, filed Nov. 16, 2010, Jason L. Craig.
U.S. Appl. No. 12/948,081, filed Nov. 17, 2010, Boris Chernov.
U.S. Appl. No. 12/948,144, filed Nov. 17, 2010, Boris Chernov.
U.S. Appl. No. 12/950,505, filed Nov. 19, 2010, David M. Garrison.
U.S. Appl. No. 12/955,010, filed Nov. 29, 2010, Paul R. Romero.
U.S. Appl. No. 12/955,042, filed Nov. 29, 2010, Steven C. Rupp.
U.S. Appl. No. 12/981,771, filed Dec. 30, 2010, James D. Allen, IV.
U.S. Appl. No. 12/981,787, filed Dec. 30, 2010, John R. Twomey.
U.S. Appl. No. 13/006,538, filed Jan. 14, 2011, John W. Twomey.
U.S. Appl. No. 13/029,390, filed Feb. 17, 2011, Michael C. Moses.
U.S. Appl. No. 13/030,231, filed Feb. 18, 2011, Jeffrey M. Roy.
U.S. Appl. No. 13/050,182, filed Mar. 17, 2011, Glenn A. Horner.
U.S. Appl. No. 13/072,945, filed Mar. 28, 2011, Patrick L. Dumbauld.
U.S. Appl. No. 13/075,847, filed Mar. 30, 2011, Gary M. Couture.
U.S. Appl. No. 13/080,383, filed Apr. 5, 2011, David M. Garrison.
U.S. Appl. No. 13/083,962, filed Apr. 11, 2011, Michael C. Moses.
U.S. Appl. No. 13/085,144, filed Apr. 12, 2011, Keir Hart.
U.S. Appl. No. 13/089,779, filed Apr. 19, 2011, Yevgeniy Fedotov.
U.S. Appl. No. 13/091,331, filed Apr. 21, 2011, Jeffrey R. Townsend.
U.S. Appl. No. 13/102,573, filed May 6, 2011, John R. Twomey.
U.S. Appl. No. 13/102,604, filed May 6, 2011, Paul E. Ourada.
U.S. Appl. No. 13/108,093, filed May 16, 2011, Boris Chernov.
U.S. Appl. No. 13/108,129, filed May 16, 2011, Boris Chernov.
U.S. Appl. No. 13/108,152, filed May 16, 2011, Boris Chernov.
U.S. Appl. No. 13/108,177, filed May 16, 2011, Boris Chernov.
U.S. Appl. No. 13/108,196, filed May 16, 2011, Boris Chernov.
U.S. Appl. No. 13/108,441, filed May 16, 2011, Boris Chernov.
U.S. Appl. No. 13/108,468, filed May 16, 2011, Boris Chernov.
U.S. Appl. No. 13/111,642, filed May 19, 2011, John R. Twomey.
U.S. Appl. No. 13/111,678, filed May 19, 2011, Nikolay Kharin.
U.S. Appl. No. 13/113,231, filed May 23, 2011, David M. Garrison.
U.S. Appl. No. 13/157,047, filed Jun. 9, 2011, John R. Twomey.
U.S. Appl. No. 13/162,814, filed Jun. 17, 2011, Barbara R. Tyrrell.
U.S. Appl. No. 13/166,477, filed Jun. 22, 2011, Daniel A. Joseph.
U.S. Appl. No. 13/166,497, filed Jun. 22, 2011, Daniel A. Joseph.
U.S. Appl. No. 13/179,919, filed Jul. 11, 2011, Russell D. Hempstead.
U.S. Appl. No. 13/179,960, filed Jul. 11, 2011, Boris Chernov.
U.S. Appl. No. 13/179,975, filed Jul. 11, 2011, Grant T. Sims.
U.S. Appl. No. 13/180,018, filed Jul. 11, 2011, Chase Collings.
U.S. Appl. No. 13/183,856, filed Jul. 15, 2011, John R. Twomey.
U.S. Appl. No. 13/185,593, filed Jul. 19, 2011, James D. Allen, IV.
Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps" , Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparoscopic Surgery; Sales/Product Literature; Apr. 2002.

(56) References Cited

OTHER PUBLICATIONS

Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.

McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.

(56) References Cited

OTHER PUBLICATIONS

Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 011750.6 dated Feb. 1, 2011.
Int'l Search Report EP 10 185386.9 dated Jan. 10, 2011.
Int'l Search Report EP 10 185405.7 dated Jan. 5, 2011.
Int'l Search Report EP 10 157500.9 dated Jul. 30, 2010.
Int'l Search Report EP 10 159205.3 dated Jul. 7, 2010.
Int'l Search Report EP 10 160870,1 dated Aug. 9, 2010.
Int'l Search Report EP 10 161596.1 dated Jul. 28, 2010.
Int'l Search Report EP 10 168705.1 dated Oct. 4, 2010.
Int'l Search Report EP 10 169647.4 dated Oct. 29, 2010.
Int'l Search Report EP 10 172005.0 dated Sep. 30, 2010.
Int'l Search Report EP 10 175956.1 dated Nov. 12, 2010.
Int'l Search Report EP 10 181034.9 dated Jan. 26, 2011.
Int'l Search Report EP 10 181575.1 dated Apr. 5, 2011.
Int'l Search Report EP 10 181969.6 dated Feb. 4, 2011.
Int'l Search Report EP 10 182022.3 dated Mar. 11, 2011.
Int'l Search Report EP 10 189206.5 dated Mar. 17, 2011.
Int'l Search Report EP 10 191320.0 dated Feb. 15, 2011.
Int'l Search Report EP 11 151509.4 dated Jun. 6, 2011.
Int'l Search Report EP 11 152220.7 dated May 19, 2011.
Int'l Search Report EP 11 152360.1 dated Jun. 6, 2011.
Int'l Search Report EP 11 161117.4 dated Jun. 30, 2011.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.
International Search Report and Written Opinion of the International Searching Authority mailed Jan. 17, 2013 from counterpart International Application No. PCT/US2012/050094 (8 pgs.).
European Search Report, issued Feb. 19, 2015, corresponding to European Application No. 12824142.9; 6 pages.

* cited by examiner

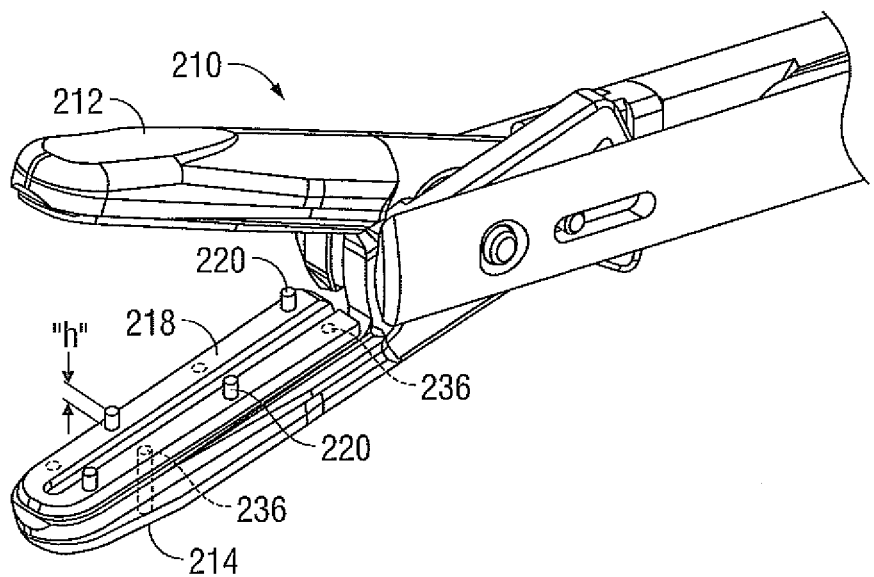
FIG. 9
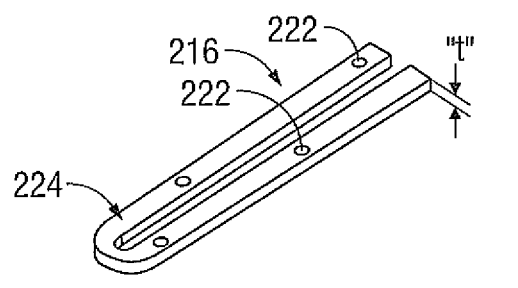 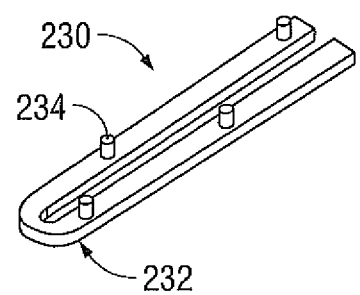
FIG. 10  FIG. 11

SURGICAL INSTRUMENTS WITH REMOVABLE COMPONENTS

BACKGROUND

1. Technical Field

The present disclosure relates generally to the field of reposable or reusable surgical instruments. In particular, the disclosure relates to instruments having separable and replaceable components to provide clean, sterile or refurbished surfaces in each instance of use.

2. Background of Related Art

Instruments such as electrosurgical forceps are commonly used in open and endoscopic surgical procedures to coagulate, cauterize and seal tissue. Such forceps typically include a pair of jaws that can be controlled by a surgeon to grasp targeted tissue, such as, e.g., a blood vessel. The jaws may be approximated to apply a mechanical clamping force to the tissue, and are associated with at least one electrode surface to permit the delivery of electrosurgical energy to the tissue. The combination of the mechanical clamping force and the electrosurgical energy has been demonstrated to join adjacent layers of tissue captured between the jaws. When the adjacent layers of tissue include the walls of a blood vessel, sealing the tissue may result in hemostasis. Thereafter, the sealed tissue may be transected by advancing a knife through the jaws. A detailed discussion of the use of an electrosurgical forceps may be found in U.S. Pat. No. 7,255,697 to Dycus et al.

In use, various tissue-contacting components of an electrosurgical forceps tend to become contaminated or degraded. For example, electrodes may become contaminated as portions of the treated tissue adhere to the tissue-contacting surfaces of the electrodes. Also, a knife blade may become dull and less effective in transecting sealed tissue after repeated use, even in a single surgical procedure. In order to provide clean electrodes and a sharp knife for a particular surgical procedure, a brand new instrument is often used. Once the procedure is complete, the used instrument is discarded.

Instruments that are reposable, or reusable for multiple procedures, reduce the instrumentation costs per procedure. Providing a reusable electrosurgical forceps, however, presents various challenges. For example, the complexity of an electrosurgical forceps tends to result in fairly labor intensive cleaning procedures to prepare the forceps for subsequent use. Improper cleaning may result in dangerous contamination being introduced surgical site. Also, some reusable forceps have removable and replaceable components to provide clean surfaces for each use. Many of these instruments require arduous disassembly and reassembly procedures that require extensive training, and may discourage use of the instrument.

SUMMARY

The present disclosure describes a surgical instrument for treating tissue. The instrument includes a handle assembly having a connector for electrically coupling the handle assembly to a source of electrosurgical energy. An end effector including a pair of opposed jaw members is operatively coupled to a distal end of the handle assembly such that one or both of the jaw members is induced to move relative to the other between open and closed positions in response to manipulation of the handle assembly. A base is supported on one of the jaw members. The base includes a mechanical mating feature, and an electrically conductive region that is in electrical communication with the connector. A selectively removable seal plate is supported on the base. The seal plate includes a mechanical mating feature complementarily engaging mechanical mating feature of the base to maintain the seal plate in position on the base during use. An electrically conductive region is provided on the seal plate, and is positioned to contact the electrically conductive region of the base when the mechanical mating features of the base and seal plate are engaged. The electrically conductive region of the seal plate is in electrical communication with an electrode surface on the seal plate. The complimentarily-engaging mechanical mating features include a pair of spaced protrusions on either the base or the seal plate, and a pair of spaced recesses open to opposing sides of the other of the base and the seal plate. The seal plate may thus be twisted onto the base.

The protrusions may be spaced in a generally longitudinal direction and may extend from the base. The recesses may be open to opposing lateral sides of the seal plate. The recesses may include undercut slots such that a head portion of each of the protrusions overhangs a lower portion of the seal plate when the protrusions engage the slots. The slots may include a tapered opening for guiding the seal plate onto the protrusions.

The seal plate may include a fastening layer constructed of an electrically insulative material and a sealing surface constructed of an electrically conductive material. The recesses may be defined in the fastening layer. The electrically conductive region of the base may be defined on one or more of the protrusions. One or more of the protrusions may extend beyond the electrode surface of the seal plate when the seal plate is coupled to the base such that the protrusion maintains a gap between the jaw members when the jaw members are moved to the closed position.

According to another aspect of the disclosure, a surgical instrument includes a handle assembly having a connector for electrically coupling the handle assembly to a source of electrosurgical energy. An end effector including a pair of opposed jaw members is operatively coupled to a distal end of the handle assembly such that one or both of the jaw members is induced to move relative to the other between open and closed positions in response to manipulation of the handle assembly. A base is supported on one of the jaw members. The base includes a mechanical mating feature and an electrically conductive region. The electrically conductive region is in electrical communication with the connector. A selectively removable seal plate is supported on the base. The seal plate includes a mechanical mating feature complementarily engaging a mechanical mating feature of the base to maintain the seal plate in position on the base during use, and an electrically conductive region positioned to contact the electrically conductive region of the base when the mechanical mating features of the base and seal plate are engaged. The electrically conductive region of the seal plate is in electrical communication with an electrode surface on the seal plate. The mechanical mating feature of the base includes at least one protrusion constructed of an electrically isolative material and extending beyond the electrode surface of the seal plate when the seal plate is coupled to the base. The protrusion thus maintains a gap between the jaw members when the jaw members are moved to the closed position.

The gap maintained may be between about 0.001 inches and about 0.006 inches. The mechanical mating feature of the seal plate may include at least through bore establishing a friction fit with the at least one protrusion, and the base may include a hole extending through the jaw member to provide access for a tool to be inserted for pressing the seal plate from the jaw member. The electrically conductive region of the base may include exposed leads of a flex circuit.

According to another aspect of the disclosure, a surgical instrument includes a handle assembly having a connector for electrically coupling the handle assembly to a source of electrosurgical energy. A pair of opposed jaw members is operatively coupled to a distal end of the handle assembly such that at least one of the jaw members is induced to move relative to the other jaw member between open and closed positions in response to manipulation of the handle assembly. At least one of the jaw members includes a base including a mechanical mating feature and a flexible circuit supported by the base. The flexible circuit includes an exposed electrically conductive region that is in electrical communication with the connector. A seal plate is supported on the base. The seal plate includes a mechanical mating feature complementarily engaging the mechanical mating feature of the base to maintain the seal plate in position on the base during use. An electrically conductive region on the seal plate is positioned to contact the electrically conductive region of the flexible circuit when the mechanical mating features of the base and seal plate are engaged.

The opposed jaw members may be operatively coupled to the distal end of the handle assembly by an elongated shaft extending therebetween. The flexible circuit may extend from the at least one jaw member proximally into the elongated shaft, and the flexible circuit may be constructed of a flexible polymer substrate in a substantially flat configuration. The flexible circuit may include a region of relatively greater flexibility to facilitate movement of the opposed jaw members between the open and closed positions.

The flexible circuit may be electrically coupled to the connector through a sliding joint defined between the at least one jaw member and the elongated shaft. The sliding joint may include an electrically conductive spring pin biased between the at least one jaw member and the elongated shaft to maintain electrical contact between the at least one jaw member and the elongated shaft during movement of the opposed jaw members between the open and closed positions.

The mechanical mating feature on the base may include an opening defined in the base, and the mechanical mating feature on the seal plate may include a post having a head portion. The head portion may be configured to snap into the opening in the base to maintain the seal plate in position on the base and to maintain electrical continuity between the seal plate and the flexible circuit.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

FIG. 9 is a perspective view of an alternate embodiment of an end effector including a jaw member configured to receive the seal plate of FIG. 10;

FIG. 10 is a perspective view of a seal plate including bores configured for engagement with stop members defined on the jaw member depicted in FIG. 9;

FIG. 11 is a perspective view of an alternate embodiment of a seal plate that includes posts configured for engagement with bores defined on a modified jaw member of FIG. 9;

DETAILED DESCRIPTION

Figure 1:
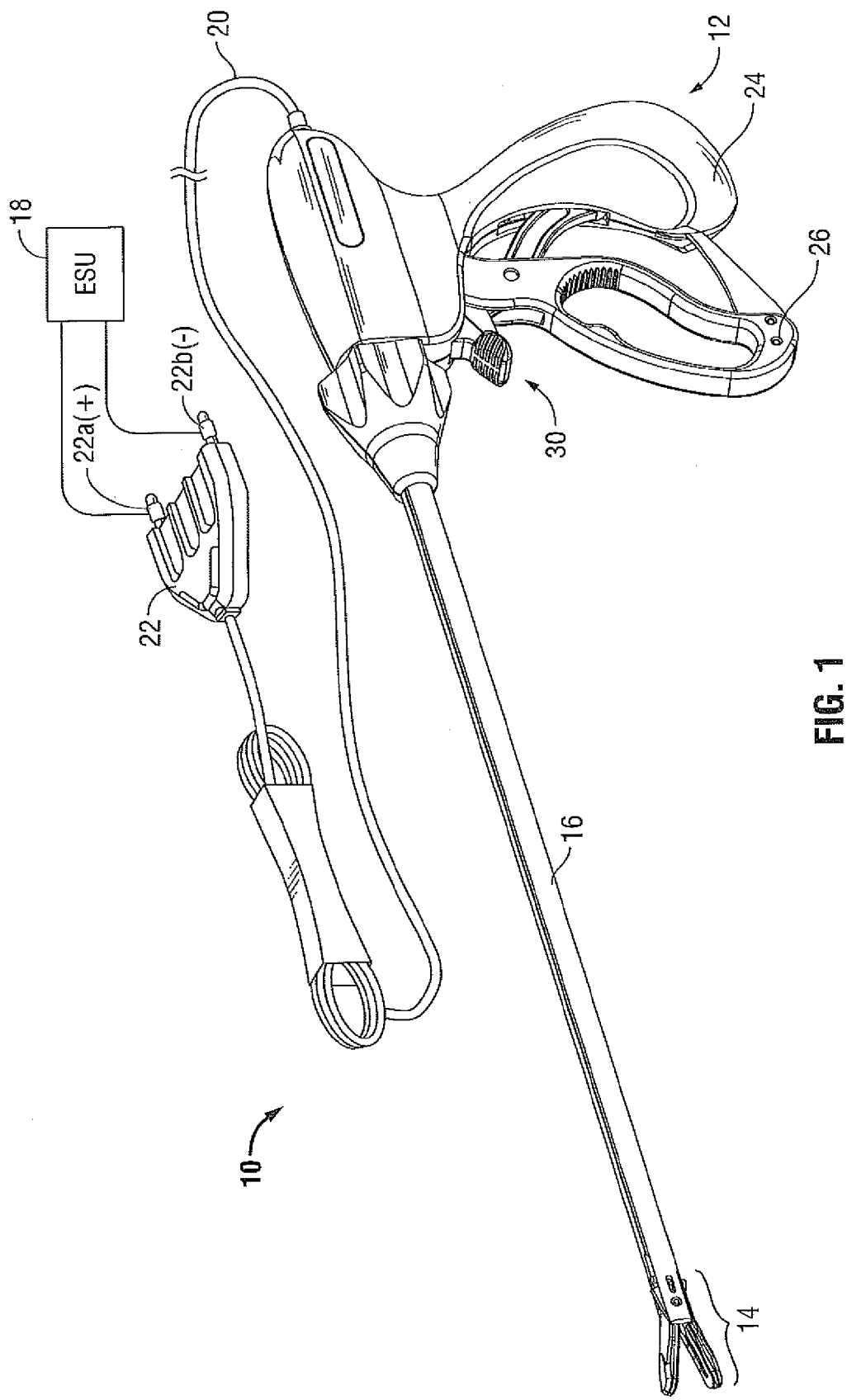
FIG. 1 is a perspective view of an endoscopic surgical instrument in accordance with an embodiment of the present disclosure having an end effector at a distal end.

Referring initially to FIG. 1, an embodiment of an electrosurgical instrument 10 is depicted. The instrument 10 includes a handle assembly 12 for remotely controlling an end effector 14 through an elongated shaft 16. Although this configuration is typically associated with instruments for use in laparoscopic or endoscopic surgical procedures, various aspects of the present disclosure may be practiced with traditional open instruments, and in connection with endoluminal procedures as well.

The instrument 10 is coupled to a source of electrosurgical energy, e.g., an electrosurgical generator 18. The generator 18 may include devices such as the LIGASURE® Vessel Sealing Generator and the Force Triad® Generator as sold by Covidien. A cable 20 extends between the handle assembly 12 and the generator 18, and includes a connector 22 for coupling the instrument 10 to the external generator 18. In other embodiments (not shown) a battery powered instrument may be provided in which a generator and connector may be internal or integral to the instrument. The connector 22 includes two prong members 22a and 22b that are dimensioned to mechanically and electrically connect the instrument 10 to opposite terminals, e.g., positive or active (+) and negative or return (−) terminals associated with the generator 18. Thus, bipolar energy may be provided through the instrument 10. Alternatively, the instrument 10 may be configured for delivering monopolar energy to the tissue. In a monopolar configuration, the instrument 10 delivers electrosurgical energy from an active terminal, e.g. (+), while a return pad (not shown) is placed generally beneath a patient and provides a return path to the opposite terminal, e.g. (−), of the generator 18.

To control the end effector 14, the handle assembly 12 includes a stationary handle 24 and movable handle 26. The movable handle 26 may be separated and approximated relative to the stationary handle 24 to respectively open and close the end effector 14. A trigger 30 is also disposed on the handle assembly 12, and is operable to extend and retract a knife 44 (see FIG. 2) through the end effector 14. A footswitch (not shown) may be provided to initiate and terminate the delivery of electrosurgical energy to the end effector 14.

Figure 2:
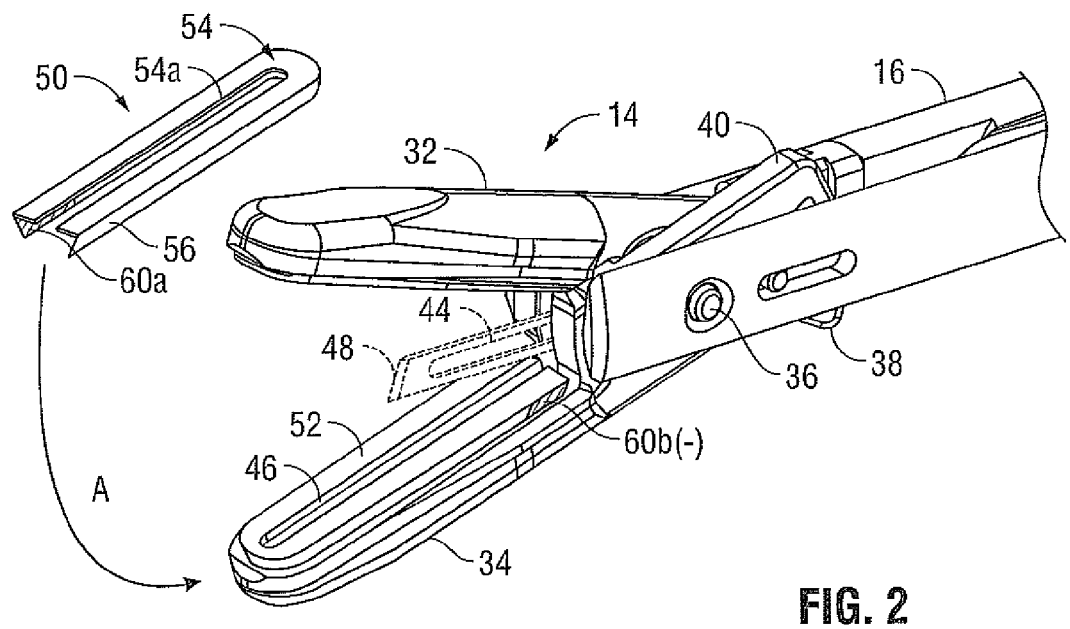
FIG. 2 is an enlarged, perspective view of the distal end of the instrument of FIG. 1 depicting a removable seal plate separated from the end effector.

Referring now to FIG. 2, end effector 14 is depicted in an open configuration. Upper and lower jaw members 32 and 34 are separated from one another such that tissue may be received therebetween. The jaw members 32, 34 are pivotally coupled to the elongated shaft 16 by a pivot pin 36 extending theretrough. To engage the pivot pin 36, the upper and lower jaw members 32, 34 include respective proximal flanges 38, 40 extending into a bifurcated distal end of the elongated shaft 16. The proximal flanges 38, 40 are operatively associated with the movable handle 26 (FIG. 1) to open and close the jaw members 32, 34. Retraction of the movable handle 26 induces the jaw members 32, 34 rotate about the pivot pin 36 to move from the open configuration to a closed configuration where the jaw members 32, 34 are closer together. When in the closed configuration, the jaw members 32, 34 may provide an appropriate pressure to tissue captured therebetween to effect a tissue seal.

Various mechanisms may be provided to operatively associate the movable handle 26 with the proximal flanges 38, 40. For example, the movable handle 26 may be coupled to a reciprocating member (see items 288, 290 in FIG. 13) that extends through the elongated shaft 16 as described in commonly owned U.S. Pat. No. 7,255,697 to Dycus et al. The reciprocating member may engage cam slots (see items 304, 306 in FIG. 13) on each of the proximal flanges 38, 40 such that the position of both of the jaw members 32, 34 changes with respect to the elongated shaft 16 as the jaw members 32, 34 are approximated. This type of motion may be characterized as "bilateral" jaw motion. Other "unilateral" constructions are also envisioned in which only one jaw member 32, 34 moves with respect to the elongated shaft 16.

A reciprocating knife 44 is selectively movable through a knife channel 46 defined through the jaw members 32, 34. The knife 44 is operatively associated with trigger 30 (FIG. 1) such that manipulation of the trigger 30 advances and/or retracts the knife 44 through the jaw members 32, 34. The knife 44 includes a sharp distal edge 48 that may be used to transect tissue sealed between the jaw members 32, 34. In some embodiments, the knife 44 may be configured to remain in a proximally retracted position, e.g. between the proximal flanges 38, 40, until the jaw members 32, 34 are moved to the closed configuration. Preventing advancement of the knife 44 while the jaw members 32, 34 are in the open configuration may prevent inadvertent cutting of unsealed tissue.

According to one embodiment of the specification, the lower jaw member 34 is configured to releasably receive a dove-tail seal plate 50 on a correspondingly shaped base 52. The seal plate 50 includes an upper sealing surface 54 with a slot 54a defined therein corresponding to the knife channel 46. The slot 54a and the knife channel 46 are optional features that may be eliminated from alternate embodiments (not shown). A tail portion 56 of the seal plate 50 protrudes laterally inward from a periphery of the sealing surface 54 to define a trapezoidal or dove-tail profile with the sealing surface 54. The tail portion 56 extends along two longitudinal sides and a distal side of the seal plate 50. A proximal side of the seal plate 50 is unobstructed by the tail portion 56 to permit the seal plate 50 to slide longitudinally onto the base 52 as indicated by arrow "A." The tail portion 56 may form a friction fit with the base 52 to mechanically couple the seal plate 50 to the jaw member 34. This type of engagement may facilitate accurate placement of the seal plate 50 while providing an effective and releasable attachment force.

The sealing surface 54 is constructed of an electrically conductive material and is configured to deliver electrosurgical energy to tissue. Thus, the sealing surface 54 may be characterized as an electrode surface. The tail portion 56 may be constructed generally of plastic, steel or another material suitable for engaging the base 52 to establish a friction-fit with the base 52. A first electrical connector 60a on the tail portion 56 is in electrical communication with the sealing surface 54. A second electrical connector 60b is in electrical communication with one of the poles or terminals, e.g., (−), of the generator 18 (FIG. 1). The two connectors 60a, 60b are positioned to electrically contact one another when the seal plate 50 is positioned on the base 52. Thus, the electrical continuity may be established between the sealing surface 54 and the terminal, e.g. (−) of the generator 18 by mechanically coupling the modular seal plate 50 to the base 52. An additional seal plate 50 may be similarly installed on the upper jaw member 32 to establish electrical continuity with the opposite terminal, e.g. (+).

Figure 3:
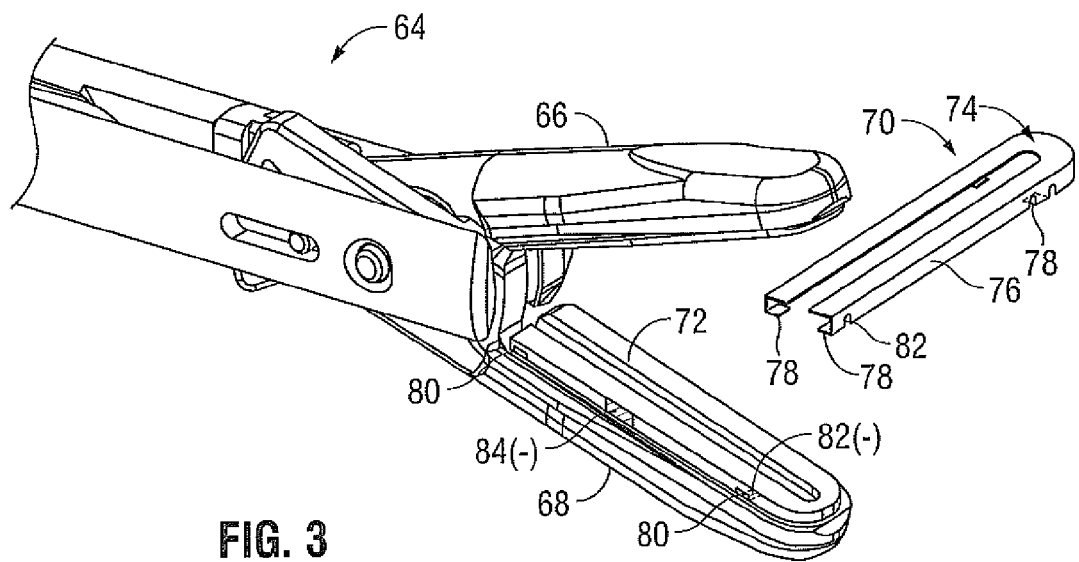
FIG. 3 is a perspective view of an alternate embodiment of an end effector with a removable seal plate separated from the end effector.

Referring now to FIG. 3, an alternate embodiment of an end effector 64 includes upper and lower jaw members 66, 68. The lower jaw member 68 is configured to releasably receive a modular snap-in seal plate 70 on a corresponding base 72. The seal plate 70 includes a sealing surface 74 and a skirt portion 76 protruding therefrom. Tabs 78 protrude inwardly from the skirt 76 for reception in slots 80 defined in the base 72. The skirt 76 includes stress-relieving notches 82 defined therein adjacent the tabs 78. The notches 82 permit the skirt 76 to flex, and to temporarily move the tabs 78 laterally outward to permit placement of the skirt over the base 72. The notches 82 may also facilitate removal of the seal plate 70 subsequent to use. The notches 82 provide surfaces for engaging a wedge (not shown) or another tool for removing the seal plate 70 from the base 72.

Electrical continuity may be established between the lower jaw member 68 and the seal plate 70 through one or more electrical connectors 82 disposed within the slots 80. The connectors 82 maintain contact with the tabs 78 when the seal plate 70 is installed on the base 72 due to the inherent resiliency of the seal plate 70. Alternatively or additionally, a connector 84 may be disposed on a lateral side of the base 72 such that the skirt 76 makes contact with the connector 84 when the seal plate 70 is installed on the base 72.

Figure 4:
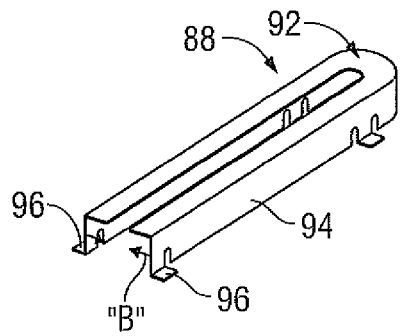
FIGS. 4 and 5 are perspective views of alternate embodiments of removable seal plates.
Figure 5:
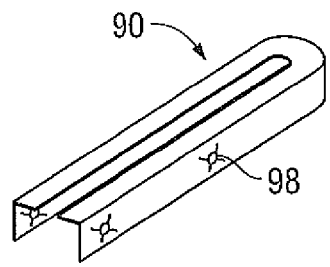

Referring now to FIGS. 4 and 5, alternate embodiments of snap-in seal plates 88 and 90 are depicted for releasable attachment to corresponding bases (not shown). Seal plate 88 is similar to seal plate 70 (FIG. 3) including a sealing surface 92 and a skirt 94 protruding therefrom. Seal plate 88 differs from seal plate 70 in that tabs 96 protrude laterally outward from the skirt 94, rather than laterally inward. Outwardly protruding tabs 96 may facilitate installation of the seal plate 88 since the skirt 94 may be flexed laterally inward, in the direction of arrows "B," to install the tabs 92 in corresponding slots (not shown). The exterior surfaces of the skirt 94 may remain accessible such that no special tool is required for installation or removal. Seal plate 90 includes detents 98 thereon for engaging corresponding mating components (not shown) on the base (not shown). The mating components may include such devices as spring loaded ball plungers positioned to engage the detents 98 when the seal plate 90 is properly installed. Electrical continuity may be established through the contact of the detents 98 with the ball plungers or other mating components.

Figure 6:
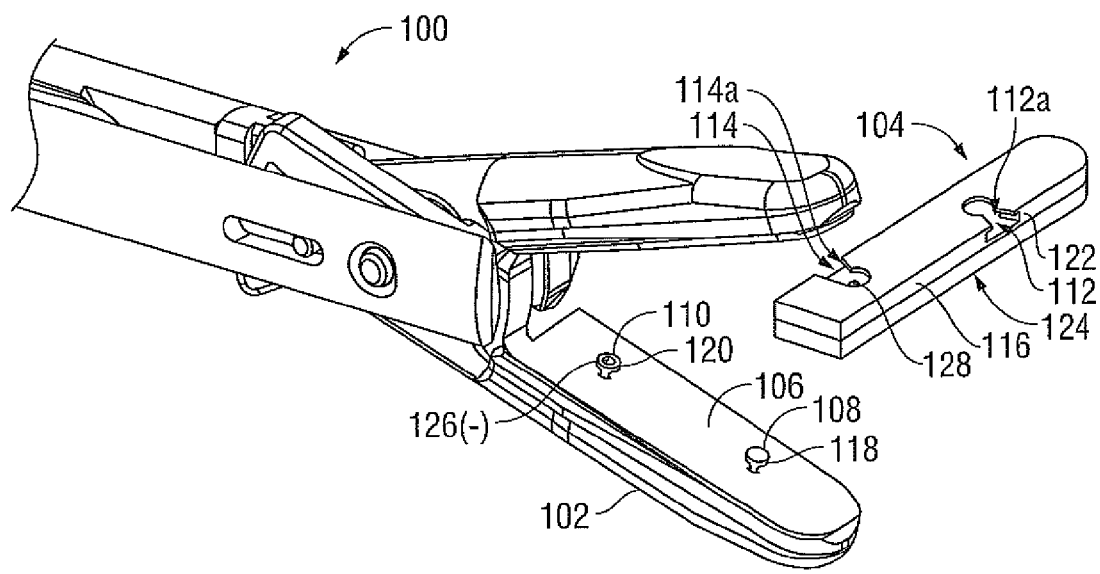
FIG. 6 is a perspective view of an alternate embodiment of an end effector including a mechanism for receiving a twist-on seal plate.

Referring now to FIG. 6, an alternate embodiment of an end effector 100 includes a jaw member 102 that is configured to releasably receive a modular, twist-on seal plate 104. The jaw member 102 includes a base 106 having a locating post 108 and a locking post 110 protruding therefrom. The locating and locking posts 108, 110 are longitudinally spaced and positioned to engage slots 112, 114 defined in a fastening layer 116 of the seal plate 104. The slots 112, 114 are undercut such that a head portion 118, 120 of each of the posts 108, 110 overhangs a lower portion 122 of the fastening layer 116. The slots 112, 114 are each open to an opposite lateral side of the seal plate 104. Thus, the seal plate 104 may be installed on the base 106 by positioning the seal plate 104 between the posts 108, 110 such that the fastening layer 116 abuts the base 106, and twisting the seal 104 such that the slots 112, 114 engage the posts 108, 110. The slots 112, 114 each include one or more tapered openings 112a, 114a to guide the slots 112, 114 onto the posts 108, 110. The slot 112 includes a taper on each longitudinal side of the opening 112a, and may be installed on the locating post 108 prior to twisting the seal plate 104 to engage the slot 114 with the locking post 110. The opening 114a of the slot 114 includes a single taper to provide clearance for the locking post 100 to enter the slot 114 as the seal plate 104 is twisted. Thus, the locating post 108 may provide a pivot for accurately guiding the slot 114 onto the locking post 110. The seal plate 104 snaps onto the base 106 when the seal plate 104 is properly located.

The seal plate 104 includes a sealing surface 124 opposite the fastening layer 116. Electrical continuity may be established between the sealing surface 124 and the jaw member 102 through one or more electrically conductive regions or connectors, e.g., connector 126 disposed on one posts, e.g., post 110. The seal plate 104 may be constructed entirely of an electrically conductive material such that electrosurgical energy may be transmitted to the sealing surface 124 when the seal plate 104 is properly installed on the base 106. Alternatively, the fastening layer 116 or other portions of the seal plate 104 may be constructed of an electrically insulative material, and an electrical connector 128 within the slot 114 may be in electrical communication with the sealing surface 124. The electrical connector 128 is configured to contact the connector 126 on the post 110 when the seal plate 104 is twisted onto the jaw member 102.

Figure 7:
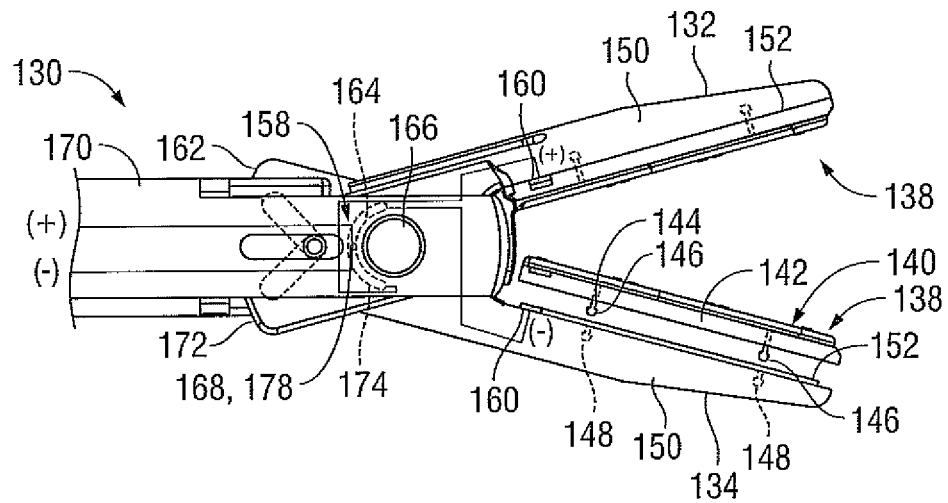
FIG. 7 is a side view of an alternate embodiment of an end effector including a pair of jaw members that are removable from an elongated shaft member, and wherein the jaw members each include a mechanism for receiving a snap-in, removable seal plate.

Referring now to FIG. 7, an alternate embodiment of an end effector 130 includes upper and lower jaw members 132, 134. The jaw members 132, 134 are each configured to releasably receive a respective seal plate 138. The seal plates 138 include a sealing surface 140, a skirt 142 and snap-in posts 144. The sealing surfaces 140 are constructed of an electrically conductive material, and are positioned to contact tissue captured between the jaw members 132, 134. The skirt 142 encircles the sealing surface 140, and may be constructed of a plastic material. The posts 144 protrude from the skirt 142 such that a head portion 146 of the posts 144 may engage a corresponding opening 148 in a base 150 defined by the respective jaw member 132, 134.

A substantially flat flex circuit 152 is disposed on each of the jaw members 132, 134 between the skirt 142 of the respective seal plate 138 and the base 150. The flex circuits 152 may be constructed as a plurality of electrically conductive pathways substantially encased in an insulative coating. The coating may include a flexible polymer substrate such as a Kapton® tape or film available from DuPont. The flex circuit 152 disposed on the upper jaw member 132 is electrically coupled the first terminal (+) of the generator 18 (FIG. 1), and the flex circuit 152 disposed on the lower jaw member 134 is electrically coupled to the second terminal (−) through an elongated shaft member 170 as described below. Exposed leads 160 on the flex circuits 152 are positioned to establish electrical continuity between the flex circuits 152 and the respective seal plates 138 when the seal plates 138 are installed to the jaw members 132, 134. The substantially flat configuration of the flex circuits 152 facilitates repeated engagement and disengagement of the selectively removable seal plates 138 with the bases 150.

The flex circuits 152 extend from their respective jaw members 132, 134 proximally into the elongated shaft member 170. Due to the flexibility of the flex circuits 152, the flex circuits 152 may withstand sufficient bending to permit movement of the jaw members 132, 134 between open and closed configurations without hindering the electrical operation of the flex circuits 152. Various portions of the flex circuits 152 may be specifically configured to permit bending, e.g., by being constructed of a relatively flexible substrate material, or by including strategic openings in the substrate material.

A sliding joint 158 is also provided to maintain electrical continuity between each of the jaw members 132, 134 and the respective terminal (+), (−) of the generator 18 (FIG. 1). A proximal flange 162 of the lower jaw member 134 includes an electrically conductive arc 164 disposed about a pivot pin 166. A spring pin 168 is disposed on an elongated shaft member 170, and is electrically coupled to the active (+) terminal of the generator 18. The spring pin 168 is biased to maintain contact with the electrically conductive arc 164, as the jaw members 132 and 134 pivot between open and closed configurations. Similarly, a proximal flange 172 of the upper jaw member 132 includes an electrically conductive arc 174 disposed about the pivot pin 166. A spring pin 178 is disposed on an elongated shaft member 170, and is electrically coupled to the return (−) terminal of the generator 18. The spring pin 178 is biased to maintain contact with the arc 174. The spring pins 168, 178 provide a releasable engagement with the jaw members 132, 134. Thus, the jaw members 132, 134 may be disassembled from the elongated shaft member 170, and replaced with a new or refurbished pair of jaw members 132, 134. Electrical continuity may be reestablished with the spring pins 168, 178 by mechanically coupling the new jaw members 132, 134 to the shaft member 170 without requiring a separate electrical assembly.

Figure 8:
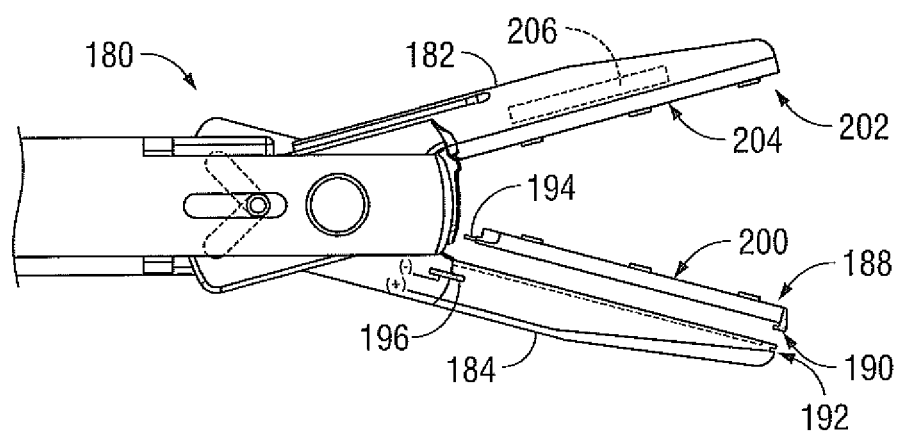
FIG. 8 is a side view of an alternate embodiment of an end effector including a removable seal plate configured to hook to a distal end of one of the jaw members and a seal plate configured for magnetic coupling to another one of the jaw members.

Referring now to FIG. 8, an alternate embodiment of an end effector 180 includes upper and lower jaw members 182, 184. The lower jaw member 184 is configured for releasable mating with a seal plate 188. The seal plate 188 includes a distal hook portion 190 for snapping into a distal recess 192 of the lower jaw member 184. A wire or round conductor 194 disposed at a proximal end of the seal plate 188 is configured to snap into trough 196 defined in the lower jaw member 184. In other embodiments (not shown), the position of the conductor 194 and trough 196 may be reversed such that a trough is defined on a removable seal plate and is configured to snap onto a conductor defined in a jaw member. The conductor 194 is electrically coupled to a sealing surface 200 such that the sealing surface 200 may be electrically coupled to a return (−) terminal of the generator 18 (FIG. 1). The distal hook portion 190 is electrically isolated from the sealing surface 200. Thus, the distal hook portion 190 may be independently coupled to the active (+) terminal of the generator 18 through the recess 192 to provide a monopolar tip to the end effector 180.

The upper jaw member 182 is configured for releasable engagement with an alternate seal plate 202. The seal plate 202 includes a sealing surface 204 that may be electrically coupled to the active (+) terminal of the generator 18. The sealing surface 204 opposes sealing surface 200 such that electrosurgical energy may be transmitted through tissue captured between the sealing surfaces 200, 204 in a bipolar manner. The monopolar tip defined by the hook portion 190 may be electrically activated independently of the bipolar sealing surfaces 200, 204.

The upper jaw member 182 includes a magnet 206 disposed therein. The magnet 206 is configured to attract the seal plate 206 and maintain the seal plate 206 in position on the jaw member 182. The magnet 206 may be used exclusively to provide a releasable locking mechanism for the seal plate 206. This type of engagement includes no moving or wearing parts. Alternatively, the magnet 206 may be employed to supplement other locking features such as hook portion 190 on the seal plate 188.

Referring now to FIGS. 9 and 10, end effector 210 includes upper and lower jaw members 212, 214 configured for releasably engaging seal plate 216. The lower jaw member 214 includes a base 218 having a plurality of stop members 220 protruding therefrom. The seal plate 216 includes a plurality of through bores 222 defined therethrough corresponding to the position of the stop members 220. The bores 222 may be placed over the stop members 220 to form a friction fit therewith to install the seal plate 216 to the base 218. The upper and lower jaw members 212, 214 may be moved to a closed configuration to seat the seal plate 216 into position. The stop members 220 may be configured to retract into the lower jaw member 214 to release the seal plate 216 from the base 218 once the seal plates are used.

The base 218 may be configured to transmit electrosurgical energy to the seal plate 216 such that a sealing surface 224 may, in turn, transmit the electrosurgical energy to tissue. The stop members 220 are constructed of an electrically insulating material, and exhibit a height "h" over the base 218. The seal plate 216 has a thickness "t" that is less than the height "h" of the stop members 220 such that the stop members 220 protrude from the sealing surface 224 when the seal plate 216 is installed. The difference between the height "h" of the stop members 220 and the thickness "t" of the seal plate 216 defines a separation or gap distance between the upper and lower jaw members 212, 214 when the jaw members 212, 214 are moved to a closed configuration. An appropriate gap distance for generating an effective tissue seal may be between about 0.001 inches and about 0.006 inches. A gap distance between about 0.002 inches and about 0.003 inches may be preferred in some instances.

The stop members 220 serve as mechanical mating features by complementarily engaging the through bores 222 to maintain the seal plate 216 in position on the base 218 during use. Other configurations are envisioned in which mechanical mating features may serve as stop members. For example, the locating post 108 described above with reference to FIG. 6 may be configured to serve as a stop member. The slot 112 defined in the seal plate 104 may be modified to extend through both the fastening layer 116 and the sealing surface 124 such that the locating post 108 could be extended to protrude beyond the sealing surface 124 to define an appropriate gap.

Referring now to FIG. 11, an alternate embodiment of a seal plate 230 includes a sealing surface 232 and a plurality of engagement posts 234 protruding from an opposite side thereof. The seal plate 230 may be constructed entirely of an electrically conductive material by construction methods including metal injection molding (MIM). The posts 234 are configured to form a friction fit with holes 236 (depicted in phantom) formed in the lower jaw member 214. The holes 236 extend through the jaw member 214 such that a tool (not shown) may be inserted through the holes 236 to press the posts 234 out of the holes 236 and remove the seal plate 230 from the base 218.

Figure 12:
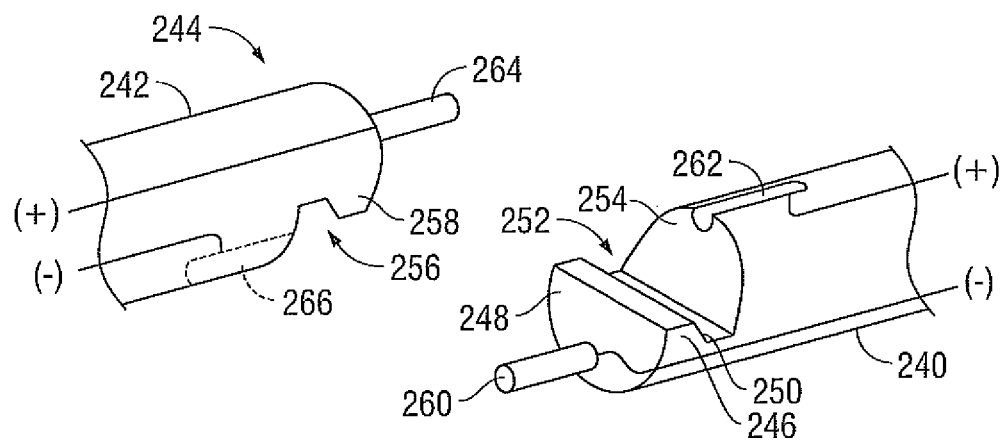
FIG. 12 is a perspective view of a wedge joint defined between two tubular members.

Referring now to FIG. 12, releasable mechanical and electrical connections may be established between tubular members 240, 242 with a wedge joint 244. A proximal tubular member 240 may be coupled to a reusable handle assembly 12 (see FIG. 1) and distal tubular member 242 may be coupled to a modular end effector 14 (see FIG. 1). Thus, the wedge joint 244 provides a mechanism for removing and replacing the entire end effector 14.

The proximal tubular member 240 includes a laterally prominent wedge 246 defined between tapered walls 248 and 250, and a laterally recessed wedge-receiving portion 252 defined between tapered walls 250 and 254. The wedge 246 and wedge-receiving portion 252 engage a wedge-receiving portion 256 and wedge 258 of distal tubular member 242 when the proximal and distal tubular members 240, 242 are laterally approximated. A friction fit may be established between the wedges 246, 258 and the respective wedge-receiving portions 256, 252 such that mechanical forces may be transmitted between the tubular members 240, 242. For example, longitudinal and rotational movement of the proximal tubular member 240 induces a corresponding motion in the distal tubular member 242.

Electrical connectivity may also be established by laterally approximating the tubular members 240, 242. The proximal tubular member 240 includes an electrically conductive pin 260 protruding from a distal end thereof and an electrically conductive pin-receiving socket or slot 262 on a lateral side thereof. The pin 260 and socket 262 may be electrically coupled to opposite terminals (+), (−) of the generator 18 (FIG. 1). The socket 262 is configured to receive an electrically conductive pin 264 protruding from a proximal end of the distal tubular member 242. The electrically conductive pin 264 may be in electrical communication with a seal plate or an electrode of the modular end effector 14 (see FIG. 1). Thus, by establishing electrical communication between the socket 262 and the pin 264, electrical connectivity may be established between the end effector 14 and an active (+) terminal of the generator 18. Similarly, the pin 260 may be electrically coupled to a socket 266 defined in the distal tubular member 242 to establish electrical continuity between the end effector 14 and a return (−) terminal of the generator 18.

Figure 13:
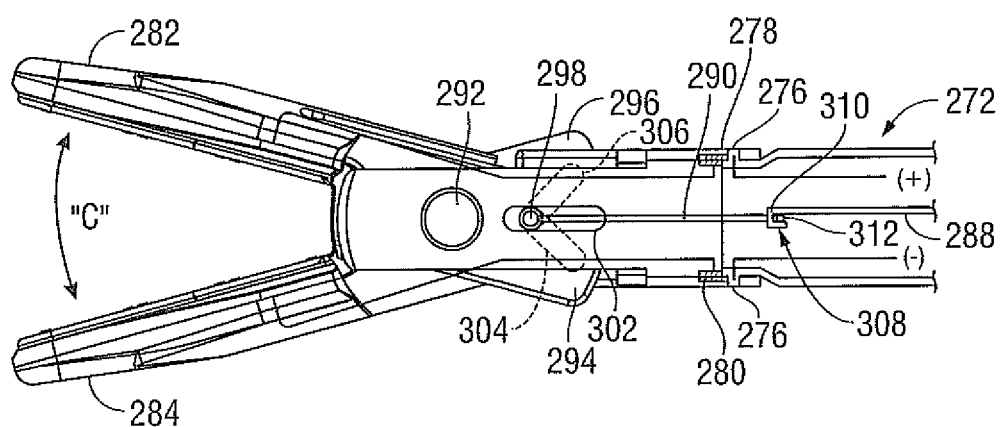
FIG. 13 is a partial, side view of an instrument including an end effector removably coupled to an elongated shaft by a bayonet coupling.

Referring now to FIG. 13, an alternative embodiment of a mechanical and electrical coupling between a modular end effector 270 and a proximal tubular member 272 is depicted. The proximal tubular member 272 includes a pair of pins 276 protruding laterally from a distal end thereof. The pins 276 form a bayonet-style engagement with a distal tubular member 278 of the end effector 270. The pins 276 are electrically coupled to opposite terminals (+), (−) of the generator 18 (FIG. 1), and engage a flex circuit 280 disposed within the distal tubular member 278. The flex circuit 280 is electrically coupled to jaw members 282, 284 such electrical continuity may be established between the jaw members 282, 284 and the generator 18.

An additional mechanical coupling is established between a reciprocating drive rod 288 extending through the tubular member 272 and a distal drive rod 290 extending through the distal tubular member 278. The drive rods 288, 290 cooperate to facilitate movement of the jaw members 282, 284 between open and closed configurations. Each of the jaw members 282, 284 is coupled to the distal tubular member 278 about a pivot pin 292 such that the jaw members 282, 284 are pivotable to a closed configuration where the jaw members 282, 284 are closer together to clamp the tissue therebetween. The jaw members 282, 284 include respective proximal drive flanges 294, 296 extending into the distal tubular member 278 where the proximal drive flanges 294, 296 engage a drive pin 298. The drive pin 298 is movably disposed in a longitudinal drive slot 302 extending through the distal tubular member 278. Each of the proximal drive flanges 294, 296 of the jaw members 282, 284 include a respective cam slot 304, 306 that engages the drive pin 298 as the drive pin 298 reciprocates through the longitudinal drive slot 302. The cam slots 302 and 304 are disposed obliquely with respect to the longitudinal drive slot 302 such that longitudinal movement of the drive pin 298 induce the jaw members 282, 284 to pivot about the pivot pin 292 in the direction of arrows "C."

The drive pin 298 is operatively associated with the distal drive rod 290, and distal drive rod 290 is operatively associated with the reciprocating drive rod 288 through a separable coupling 308. The coupling 308 is defined by a J-shaped end 310, 312 of each of the drive rods 288, 290 engaging the other J-shaped end 310, 312. The reciprocating drive rod 288 may be operatively associated with movable handle 26 (FIG. 1) to induce longitudinal motion in the drive rod 288. This longitudinal motion may be transmitted to the distal drive rod 290 through the coupling 308. This longitudinal motion is transmitted to the drive pin 298 to open and close the jaw members 282, 284.

Figure 14:
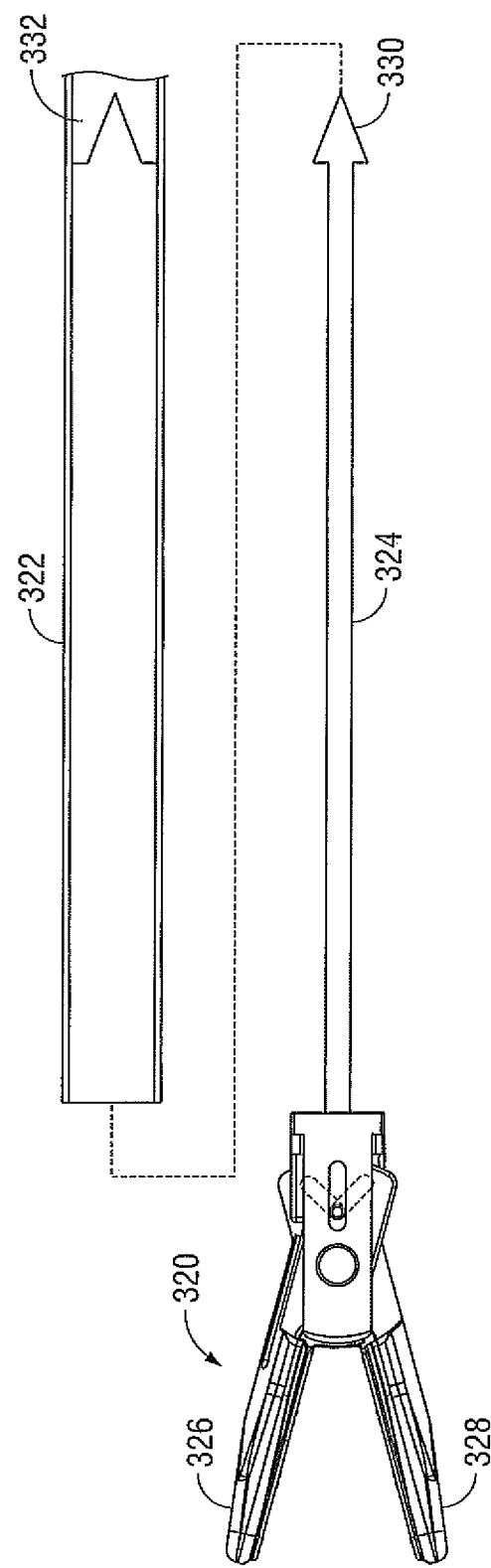
FIG. 14 is a partial side view of an instrument including electrical and mechanical coupling mechanisms disposed at a proximal end of an elongated shaft.

Referring now to FIG. 14, a modular end effector 320 is configured for removable coupling to an elongated shaft 322. A drive assembly 324 extends proximally from the end effector 320, and may include reciprocating members for actuating jaw members 326, 328 and/or a reciprocating knife 44 (see FIG. 2). The drive assembly 324 may also include electrical conductors (not shown) configured for the transmission of electrosurgical energy therethrough to provide electrosurgical energy to the jaw members 326, 328. A mechanical and electrical coupling member 330 is disposed at a proximal end of the drive assembly 324, and is configured for releasable engagement with a corresponding coupling member 332 disposed within the elongated shaft 322.

The coupling member 332 may be mechanically coupled to one or more actuators such as movable handle 26 or trigger 30 (see FIG. 1) such that mechanical motion may be imparted to the end effector 320 through the drive assembly 24. Similarly, the coupling member 332 may be electrically coupled to electrosurgical generator 18 (FIG. 1) such that electrosurgical energy may be delivered to the jaw members 326, 328. To install the modular end effector 320 to the elongated shaft, the coupling member 330 is inserted into the open distal end of the elongated shaft 322 and advanced until engaging the coupling member 332. The corresponding coupling members 330, 332 may be mechanically and electrically coupled to one another through a snap-fit engagement, a twist-to-lock arrangement or another mating mechanism.

This modular configuration may be convenient for an operator to assemble since the end effector 320 is provided in a fully assembled condition. Many of the relatively small or delicate components of the end effector 320, such as pivot pin 292 (FIG. 13), drive pin 298 (FIG. 13) and knife 44 (FIG. 2), are preassembled to form a substantial modular unit that is convenient to manipulate by hand. Knife 44 may be protected from damage during installation of the end effector 320 due in part to its retracted position within the jaw members 326, 328. This modular configuration also locates the electrically engaging components, e.g., corresponding coupling members 330, 332, at a proximal location substantially spaced from a wet surgical site during use. Proximally locating the electrically engaging components may preserve functionality over time, and may facilitate cleaning of a modular system.

Although the foregoing disclosure has been described in some detail by way of illustration and example, for purposes of clarity or understanding, it will be obvious that certain changes and modifications may be practiced within the scope of the appended claims.

What is claimed is:

1. A surgical instrument, comprising:
   a handle assembly including a connector for electrically coupling the handle assembly to a source of electrosurgical energy;
   an end effector including a pair of opposed jaw members operatively coupled to a distal end of the handle assembly such that at least one of the jaw members is induced to move relative to the other jaw member between open and closed positions in response to manipulation of the handle assembly;
   a base supported on at least one of the jaw members, the base including a mechanical mating feature and an electrically conductive region thereon, the electrically conductive region in electrical communication with the connector; and
   a selectively removable seal plate supported on the base, the seal plate including a mechanical mating feature complementarily engaging the mechanical mating feature of the base to maintain the seal plate in position on the base during use, and an electrically conductive region positioned to contact the electrically conductive region of the base when the mechanical mating features of the base and seal plate are engaged, the electrically conductive region in electrical communication with an electrode on the seal plate;
   wherein the complimentarily-engaging mechanical mating features includes a pair of spaced protrusions on one of the base and the seal plate, and a pair of spaced recesses open to opposing sides of the other of the base and the seal plate such that the seal plate may be twisted onto the base, wherein the protrusions are spaced in a generally longitudinal direction and extend from the base, and wherein the recesses are open to opposing lateral sides of the seal plate.

2. The surgical instrument according to claim, 1 wherein the recesses include undercut slots such that a head portion of each of the protrusions overhangs a lower portion of the seal plate when the protrusions engage the slots.

3. The surgical instrument according to claim 2, wherein the recesses include a tapered opening defined therein configured to guide the seal plate onto the protrusions.

4. The surgical instrument according to claim, 1 wherein the seal plate includes a fastening layer constructed of an electrically insulative material and a sealing surface constructed of an electrically conductive material, and wherein the recesses are defined in the fastening layer.

5. The surgical instrument according to claim 4, wherein the electrically conductive region of the base is defined on at least one of the protrusions.

6. The surgical instrument according to claim 1, wherein at least one of the protrusions of the base extends beyond the electrode surface of the seal plate when the seal plate is coupled to the base such that the protrusion maintains a gap between the jaw members when the jaw members are moved to the closed position.

* * * * *